| United States Patent [19] | [11] | 4,348,300 |
|---|---|---|
| McCartney et al. | [45] | Sep. 7, 1982 |

[54] STABILIZATION OF SODIUM DISPERSION

[75] Inventors: Robert F. McCartney, Wilmington, Del.; Nicholas Nazarenko, West Chester, Pa.

[73] Assignee: E. I. Du Pont de Nemours and Company, Wilmington, Del.

[21] Appl. No.: 173,098

[22] Filed: Jul. 28, 1980

[51] Int. Cl.$^3$ .............................................. B01J 13/00
[52] U.S. Cl. ................................ 252/309; 260/665 R; 568/7
[58] Field of Search ...................... 260/665 R; 252/309

[56] References Cited

U.S. PATENT DOCUMENTS

| 2,394,608 | 2/1946 | Hansley ........................... 260/665 R |
| 3,187,054 | 6/1965 | Willcockson et al. ................... 568/6 |
| 3,419,384 | 12/1968 | Rembaum et al. ............... 260/665 R |
| 3,723,536 | 3/1973 | Steubinger et al. .................... 568/17 |
| 3,903,184 | 9/1975 | Gerberding et al. ........... 260/665 R |
| 4,045,495 | 8/1977 | Nazarenko et al. ..................... 568/6 |
| 4,046,815 | 9/1977 | Nazarenko et al. ..................... 568/6 |

Primary Examiner—Helen M. S. Sneed

[57] ABSTRACT

Agglomeration of dispersions of an alkali metal in an organic liquid is reduced by adding at least about 2.5% of an aryl halide, e.g., chlorobenzene.

5 Claims, No Drawings

STABILIZATION OF SODIUM DISPERSION

BACKGROUND OF THE INVENTION

1. Field of the Invention

The present invention is directed to an improved process for reducing the agglomeration of finely divided alkali metal particles dispersed in an organic liquid and, more particularly, to a process for preparing finely divided sodium dispersed in an organic liquid using an aryl halide to prevent or reduce agglomeration of the dispersion.

2. Description of the Prior Art

Common methods for reducing particle settling and reagglomeration of alkali metal dispersions involve the use of a soap-types of material as set forth, for example, in U.S. Pat. No. 2,394,608 issued on Feb. 12, 1946.

A method for reducing or eliminating agglomeration of alkali metal dispersion in an inert organic liquid is disclosed in U.S. Pat. No. 2,597,257 issued on Dec. 18, 1951 and involves the use of two compounds which add together to form complex addition compounds that reduce or prevent agglomeration of dispersion. Compounds include alkali metal alkoxides and alkali metal organic compounds in which an alkali metal atom is directly attached to an allylic residue. Methanol and monochlorobenzene are disclosed as two compounds which react in the presence of sodium to form the addition product of sodium methylate with sodium phenyl which addition product is taught to decrease agglomeration.

U.S. Pat. No. 3,723,536 issued on Mar. 27, 1973 discloses a process for the synthesis of triaryl phosphines by reaction of an aryl halide with a phosphorus halide using a finely divided alkali metal which has been modified by the addition of either a triaryl phosphine and/or an aryl halide to control the rate of reaction and distribution of products. While chlorobenzene is disclosed as one of the possible additives, the patentees do not discuss the effect, if any, the addition of the aryl halide and/or the triaryl phosphine has on the condition of the particles in the sodium dispersion. The patentees teach that less than 5% by weight of either additive should be employed and preferably from 0.5-1% by weight because greater amounts, especially of the aryl halide, result in two vigorous a reaction and the formation of undesired by-products.

The process of the present invention is particularly applicable to the preparation of triarylboranes as disclosed in U.S. Pat. No. 4,046,815 issued on Sept. 6, 1977. This patent discloses the preparation of triarylboranes by reacting a finely divided alkali metal, an aryl halide and an orthoborate ester; contacting the reaction product with water to form the sodium hydroxide salt of a triarylborane and converting the salt to the borane.

SUMMARY OF THE INVENTION

The present invention involves the reducing of agglomeration of finely divided alkali metal particles which are dispersed in an inert organic liquid. The process consists essentially or consists of introducing at least about 2.5% and preferably 2.5–5% by weight based upon the weight of the alkali metal of an aryl halide into the organic liquid before the dispersion reaches a condition where agglomeration can occur.

One specific embodiment in the present invention is an improvement in the process for the preparation of triarylboranes wherein an alkali metal, an aryl halide and an orthoborate ester are reacted in an inert organic liquid and wherein the alkali metal is introduced as a dispersion of finely divided particles in an inert organic liquid which is the same organic liquid that is used in the reaction. At least about 2.5% by weight based upon the weight of the alkali metal in the dispersion of an aryl halide is added, preferably during the preparation of the dispersion and before the dispersion is contacted with the other reactants, whereby any agglomeration of the alkali metal particles is substantially reduced or eliminated. The preferred inert organic liquids are cyclohexane, benzene, toluene and mixtures of the foregoing. The preferred aryl halide is chlorobenzene.

DETAILED DESCRIPTION OF THE INVENTION

The alkali metals to which the process of the present invention can be applied include sodium and potassium in the form of a dispersion which is preferably prepared by contacting the molten alkali metal in an inert organic liquid under high shear, for example, by the use of a bullet mixer (a static dispersing device).

The inert organic liquid in which the alkali metal is dispersed includes a variety of compounds, including singly or in mixture, branched or unbranched alkanes having 5 to 10 carbon atoms, e.g., pentane, hexane, heptane, octane, decane, and 3-methylpentane; cycloalkanes having 5 to 10 carbon atoms, e.g., cyclohexane, methylcyclohexane, cyclooctane, cyclopentane; alkenes having 5 to 10 atoms and cycloalkenes having 5 to 10 carbon atoms wherein the unsaturation does not react with the alkali metal. If the dispersion is used directly for the preparation of triarylboranes according to the procedure herein described the unsaturation should not react with the aryl halide or the orthoester.

The aryl halide which is added according to the process of the present invention to prevent or reduce agglomeration can be any halogen substituted organic which is compatible with the system and is preferably one which is itself a reactant in subsequent processing steps. More than one aryl halide can be present. The aryl halides which are preferred in the present invention are those wherein the aryl group has 6 to 12 carbon atoms. In addition to halogen substituents, the aryl halide may be substituted with one or more groups either the same or different which are selected from the groups consisting of alkyl groups havng 1 to 12 carbon atoms, alkenyl groups having 2 to 12 carbon atoms, aryl groups having 6 to 12 carbon atoms, alkoxy groups having 1 to 12 carbon atoms and amino groups having the formula —$NR_2$ where R is hydrogen or the above-mentioned substituent groups except halogen. Examples of suitable aryl halides include chlorobenzene, bromobenzene, 2-chlorotoluene, 4-chlorotoluene, 4-chlorobiphenyl and the like. Chlorobenzene is the preferred aryl halide.

The point of addition of the aryl halide to the organic liquid containing the finely divided alkaline metal particles is not critical so long as the aryl halide is present when the dispersion reaches a condition where agglomeration is possible. Such a condition could be, for example, when the temperature of the dispersion is reduced from that at which the dispersion is made to a temperature at which the dispersion is introduced into subsequent processing steps. It is preferred to introduce the aryl halide into the organic liquid before introduction and subsequent dispersion of the alkali metal.

The amount of aryl halide introduced into the organic liquid can vary over a wide range provided that at least about 2.5% by weight based upon the weight of the alkali metal is present in the organic liquid. The preferred range of concentration is about 2.5–5% but concentrations up as high as about 25% can also be employed. In one preferred embodiment of the present invention the aryl halide employed is the same aryl halide which is subsequently introduced into reaction with isopropylorthoborate, additional aryl halide and sodium in the manufacture of triarylborane.

In addition to stabilizing the dispersion of alkali metal it has also been determined that the presence of the aryl halide produces a more finely divided, highly reactive dispersion.

The following examples are presented to illustrate but not to restrict the present invention. Parts and percentages are by weight unless otherwise noted.

EXAMPLES 1 AND 2 AND COMPARATIVE A AND B

The apparatus employed consisted of a 500 ml 3-neck flask equipped with a 3/16" in diameter × 14" long stainless steel stirring rod fastened with a ¾" Cruciform impellar. The rod was connected to a variable high-speed motor. In each of the experiments the flask was charged with 100 ml of molecular sieve dried reagent grade toluene, 15 grams of freshly cut sodium pieces and varying amounts of anhydrous reagent grade chlorobenzene as indicated in Table I. After the charge was completed, the pot temperature was increased to 110° C. until the sodium was melted following which the contents of the flask were stirred at approximately 9000 rpm for a period of 10 minutes to form the dispersion. The heat was then removed and the agitator speed reduced to about 1000 rpm. The contents of the flask were then cooled to 45° C. and the condition of the dispersion was noted. The contents of the flask were then discharged under an inert atmosphere to a filter and the size of the sodium was noted. The results are recorded in the Table.

TABLE

| Example No. | Aryl Halide (%) | Appearance of Dispersion | Particle Size (Microns) |
|---|---|---|---|
| 1 | 2.5 | Fine Powder | 15–20 |
| 2 | 4.0 | Fine Powder | 15–20 |
| Comparative | | | |
| A | 0 | Agglomerated | 35–40 |
| B | 1.4 | Agglomerated | 35–40 |

Toluene was employed in the foregoing examples for convenience since its boiling point lends itself to the use of non-pressurized equipment. Organic liquids such as cyclohexane and the like can be substituted for toluene with equivalent results.

We claim:

1. A process for reducing agglomeration of finely divided alkali metal particles which are dispersed in an inert organic liquid which consists essentially of introducing at least about 2.5% by weight based upon the weight of the alkali metal of an aryl halide into said organic liquid before the dispersion reaches a condition where agglomeration can occur.

2. The process of claim 1 wherein the inert organic liquid is selected from the class consisting of cyclohexane, benzene, toluene and mixtures thereof and the aryl halide is chlorobenzene.

3. The process of claim 1 wherein 2.5–5% by weight of aryl halide is introduced.

4. The process of claim 1 wherein the dispersion is prepared using molten alkali metal and the aryl halide is present before the resultant dispersion is cooled to less than 45° C.

5. The process of claim 2 wherein the chlorobenzene is added to the organic liquid prior to or during the formation of the dispersion.

* * * * *